(12) United States Patent
Guadliana et al.

(10) Patent No.: US 6,372,781 B1
(45) Date of Patent: *Apr. 16, 2002

(54) COMPOUNDS FOR TREATING GASTRODUODENAL DISEASES

(75) Inventors: Mark A. Guadliana, Stonington; Liang H. Huang, East Lyme; Takushi Kaneko, Guilford; Paul C. Watts, Mystic, all of CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/588,889

(22) Filed: Jun. 7, 2000

Related U.S. Application Data

(63) Continuation of application No. 08/765,437, filed as application No. PCT/IB95/00483 on Jun. 15, 1995, now Pat. No. 6,174,710, which is a continuation of application No. 08/287,977, filed on Aug. 9, 1994, now abandoned.

(51) Int. Cl.[7] ............................................. A61K 31/365
(52) U.S. Cl. ...................... 514/451; 435/118; 435/119; 514/456; 549/264
(58) Field of Search .................. 435/118, 119; 514/451, 456; 549/264

(56) References Cited

U.S. PATENT DOCUMENTS 6,174,710 B1 * 1/2001 Guadliana et al. .......... 435/118

OTHER PUBLICATIONS

Arnone et al., Phytochemistry, 1990, 29, 613–616.
Lee et al., Infection and Immunity, 1993, 61, 1601–1610.
O'Connor et al., Postgraduate Medical Journal, 1992, 68, 549–557.
Swinyard et al., Remington's Pharmaceutical Sciences, Gennaro, A.R., Ed. (Philadelphia College of Pharmacy and Science, Philadelphia, 1990), Chpt. 66, 1317–1329.
Graham et al., Annals of Internal Medicine, 1992, 116, 705–708.
Banerjee et al., Design of Prodrugs, Bundgard, H., Ed., (Elsevier, New York, 1985) 121–126.
Sande et al., Goodman and Gilman's The Pharmacological Basis of Therapeutics, Gilman, A. G., Ed., (Pergamon, New York, 1990) 8th Ed., 1117–1118, 1130, 1131.

* cited by examiner

*Primary Examiner*—Richard L. Raymond
(74) *Attorney, Agent, or Firm*—Peter C. Richardson; Gregg C. Benson; Robert T. Ronau

(57) ABSTRACT

Spirolaxine, the compound of formula (I) wherein R is H, and the novel compounds of formula (I) wherein R is ($C_1$–$C_5$) alkyl or $CH_3(CH_2)_nCO$ and n is 1, 2, 3 or 4 are useful in treating gastroduodenal diseases such as gastric ulcers, duodenal ulcers and gastric cancer caused by *Helicobacter pylori*. Spirolaxine and spirolaxine methyl ether are isolated from the fermentation of *Sporotrichum pruinosum* ATCC 74278. Spirolaxine and the compounds of formula (I) are also useful in combination with $H_2$ antagonist, colloidal bismuth subcitrate and other antibiotics.

(I)

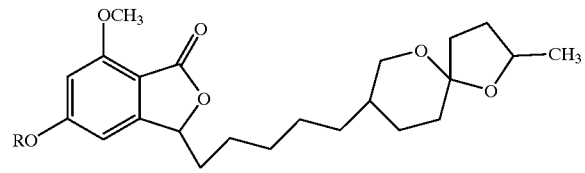

12 Claims, No Drawings

COMPOUNDS FOR TREATING GASTRODUODENAL DISEASES

This is a continuation of application Ser. No. 08/765,437, filed on Jan. 16, 1997, now U.S. Pat. No. 6,174,710, entitled Spirolaxine Derivatives For Treating Gastroduodenal Diseases which is the national stage under 35 U.S.C. §371 (c) of International Patent Application No. PCT/IB95/00483, filed Jun. 15, 1995, entitled Spirolaxine Derivatives For Treating Gastroduodenal Diseases, which is a continuation of U.S. patent application Ser. No. 08/287,977, filed Aug. 9, 1994, entitled Compounds For Treating Gastroduodenal Diseases, now abandoned.

BACKGROUND OF THE INVENTION

This invention relates to compounds of the formula (I),

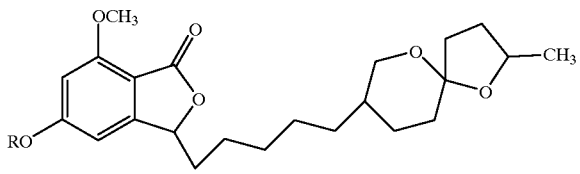

(I)

wherein R is ($C_1$–$C_5$) alkyl or $CH_3(CH_2)_nCO$—; and n is 1, 2, 3 or 4, which are useful in the treatment of diseases, disorders and adverse conditions caused by *Helicobacter pylori* and are particularly useful in the treatment of gastroduodenal disorders, diseases and adverse conditions caused thereby. This invention further relates to a method of treating *Helicobacter pylori* induced disorders, diseases and adverse conditions and particularly gastroduodenal disorders, diseases and adverse conditions in a mammal comprising administering to said mammal the compound of formula (II),

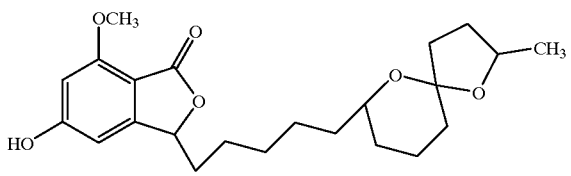

(II)

hereinafter referred to as spirolaxine.

Spirolaxine is a known antibiotic which can be isolated from the microorganism *Chiysosporium pruinosum* ATCC 15155. Spirolaxine is reported to have weak bacteriostatic activity against *Bacillus cereus, Bacillus subtilis* and *Escherichia coli*. Arnone et al., Phytochemistry, 1990, 29, 613–616. Further, spirolaxine is reported to have no antifungal activity against *Aspergillus niger, Botrytis cinerea, Cladosporium cucumerinum, Ophiostoma ulmi* and *Saccharomyces cerevisiae*. Arnone et al., Phytochemistry, 1990, 29, 613–616.

Gastric and duodenal ulcers affect a significant portion of the human population worldwide. Currently, the usual treatment for both gastric and duodenal ulcers involves treatment of the patient with $H_2$ blockers. While generally effective in healing ulcers, ulcer relapse occurs in up to 90% of patients within a year of discontinuing $H_2$ blocker therapy. O'Connor, H. J., Postgraduate Medical Journal, 1992, 68, 549–57. Thus, patients must continue the treatment for many years or risk a recurrence of the ulcer. It is now known that ulcer healing drugs such as colloidal bismuth subcitrate (CBS) are helicobactericidal and as such CBS is used in combination with $H_2$ blockers to treat ulcers. O'Connor, ibid. Additionally, CBS, an $H_2$ blocker and amoxicillin have been used in combination to treat ulcer patients. O'Connor, ibid.

*Helicobacter pylori* has recently been demonstrated to be a major causative agent in gastric and duodenal ulcers and other gastroduodenal disorders, diseases and adverse conditions. Thus, antibiotic therapy to eliminate *Helicobacter pylori* from the gastroduodenal tract would remove the root cause of said gastroduodenal disorders, diseases and adverse conditions and eliminate the need for an ulcer patient to continue long and costly treatment with $H_2$ blockers and the like. None of the foregoing treatments are capable of 100% eradication of *Helicobacter pylori*.

Applicants have now found that spirolaxine and the spirolaxine ethers of the instant invention are potent helicobactericidal compounds. A helicobactericidal compound is a compound which kills *Helicobacter pylori*. Therefore spirolaxine and the spirolaxine ethers of formula (I) of the instant invention possess utility in treating gastroduodenal disorders, diseases and adverse conditions and particularly in treating gastric and duodenal ulcer and preventing gastric cancer.

SUMMARY OF THE INVENTION

This invention is directed to a compound of the formula (I),

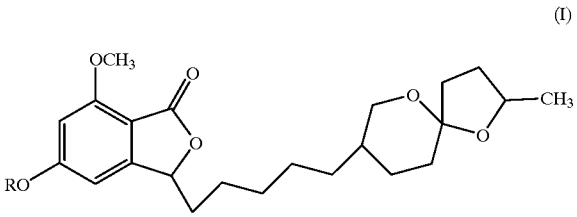

(I)

wherein:
R is ($C_1$–$C_5$) alkyl or $CH_3(CH_2)_nCO$—; and n is 1, 2, 3 or 4.

This invention is particularly directed to the compound of formula (I) wherein R is methyl.

This invention is also directed to a method for treating a mammal suffering from a *Helicobacter pylori* induced disorder, disease or adverse condition comprising administering an effective amount of a compound of formula (I) hereinabove or the compound of formula (II),

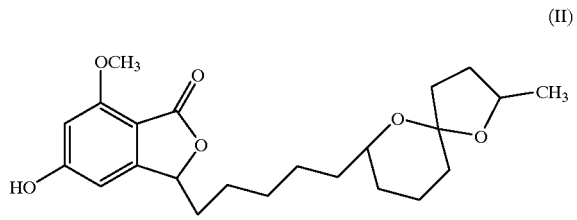

(II)

also known as spirolaxine, or a pharmaceutical composition thereof.

This invention is particularly directed to a method as described in the preceding paragraph comprising treating said disorder, disease or adverse condition with an effective amount of spirolaxine or a pharmaceutical composition thereof.

This invention is more particularly directed to a method as described in the preceding paragraph wherein said gastroduodenal disorder, disease or adverse condition is gastric ulcer, duodenal ulcer or gastric cancer.

This invention is still more particularly directed to a method of treating a mammal suffering from a duodenal ulcer comprising administering to said mammal an effective amount of spirolaxine or a pharmaceutical composition thereof.

This invention also provides a method of treating a mammal suffering from a *Helicobacter pylori* induced disorder, disease or adverse condition comprising administering to said mammal an effective amount of a combination comprising spirolaxine or a compound of formula (I) and an $H_2$ blocker.

This invention further provides a method of treating a mammal suffering from a *Helicobacter pylori* induced disorder, disease or adverse condition comprising administering to said mammal an effective amount of a combination comprising spirolaxine or a compound of formula (I), an $H_2$ blocker and colloidal bismuth subcitrate.

This invention further provides a method of treating a mammal suffering from a *Helicobacter pylori* induced disorder, disease or adverse condition comprising administering to said mammal an effective amount of a combination comprising spirolaxine or a compound of formula (I), an $H_2$ blocker and an antibiotic.

Further, this invention provides a pharmaceutical composition comprising a compound of formula (I) and a pharmaceutically acceptable carrier.

Yet further, this invention provides a pharmaceutical composition for use in treating *Helicobacter pylori* induced disorders, diseases or adverse conditions comprising a *Helicobacter pylori* treating effective amount of spirolaxine and a pharmaceutically acceptable carrier.

Still further, this invention provides a pharmaceutical composition for use in treating *Helicobacter pylori* induced disorders, diseases or adverse conditions comprising an effective amount of a combination of spirolaxine or a compound of formula (I), an $H_2$ blocker and a pharmaceutically carrier.

This invention also provides a pharmaceutical composition for use in treating *Helicobacter pylori* induced disorders, diseases or adverse conditions comprising an effective amount of a combination of spirolaxine or a compound of formula (I), an $H_2$ blocker, colloidal bismuth subcitrate and a pharmaceutically acceptable carrier.

This invention still further provides a pharmaceutical composition for use in treating *Helicobacter pylori* induced disorders, diseases or adverse conditions comprising an effective amount of a combination of spirolaxine or a compound of formula (I), an $H_2$ blocker, an antibiotic and a pharmaceutically acceptable carrier.

This invention also provides a process for preparing a compound of formula (I),

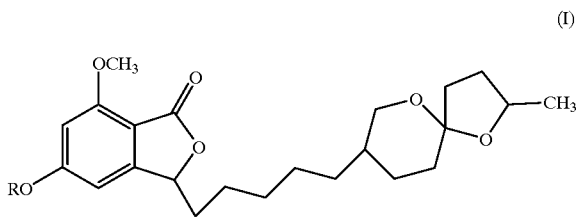

wherein R is $(C_1–C_5)$ alkyl or $CH_3(CH_2)_nCO$ and n is 1, 2, 3 or 4 comprising, when R is $(C_1–C_5)$ alkyl, reacting a compound of the formula (II),

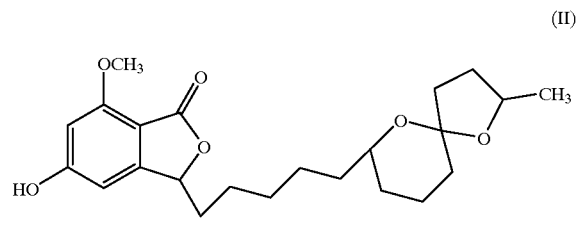

with a $(C_2–C_5)$alkyl halide in an alcohol solvent in the presence of a base; and (b) when R is $CH_3(CH_2)_nCO$ and n is 1, 2, 3 or 4, reacting a compound of the formula (II),

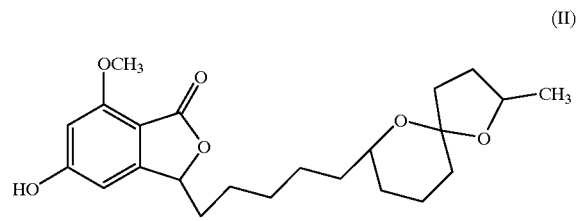

with an acyl halide in aqueous alkali.

Still further, this invention provides a process for preparing the compound of formula (II) and the compound of formula (I) wherein R is methyl comprising fermenting a culture of *Sporotrichum pruinosum* ATCC 74278 and isolating said compound of formula (II) or compound of formula (I) wherein R is methyl in substantially pure form.

With respect to the compounds of formulae (I) and (II) of this invention, it is to be understood that there are stereoisomeric forms of said compounds such as optical isomers due to asymmetric carbon atoms and that said stereoisomeric forms are also included within the scope of this invention.

DETAILED DESCRIPTION OF THE INVENTION

The present invention is readily carried out. Thus, the compound of formula (I) wherein R is methyl and the compound of formula (II) are prepared by fermentation of the microorganism *Chrysosporium pruinosum* ATCC 15155 and subsequent isolation from the fermentation broth. *Chrysosporium* pruinosum ATCC 15155 is also named *Sporotrichum pruinosum* ATCC 15155, as defined by Stapers, Studies in Mycology, 1984, 24, 105.

A lyophilized sample of *Sporotrichum pruinosum* FD 29414 was deposited with the American Type Culture Collection, 12301 Parklawn Drive, Rockville, Md., 20852, U.S.A., under the terms of the Budapest Treaty on Mar. 18, 1994. This newly deposited culture was given the new deposit number of ATCC 74278. All restrictions on the availability to the public of the microorganism culture so deposited will be irrevocably removed upon the issuance of a patent from this specification.

*Chrysosporium pruinosum* ATCC 15155 and *Sporotrichum pruinosum* ATCC 74278 refer to the same microorganism and can be obtained from the American Type Culture Collection (ATCC). The culture is smear-inoculated separately onto potato dextrose agar (PDA), malt extract agar (MEA) and cornmeal agar (CM) and the plates are incubated at 28° C. for two weeks in an incubator. The growth on PDA and MEA is good to excellent and on CM is moderate to good. On all media the colonies are white, floccose to fluffy, with a colorless reverse, attaining a diameter of 8.5 cm in two weeks. The vegetative hyphae are 2 to 7 $\mu$m wide and are septate and branched. The conidiophores consist of two to three levels of branches. The conidiophores are hyaline and smooth, having the same appearance as the vegetative hyphae; the conidiophores are 22 to 160 $\mu$m long and have a diameter of 3 to 4 $\mu$m. The primary branches of the conidiophores form at a wide angle to the conidiophore and are mostly monopodially arranged; the primary branches are often curved toward the tip and are hyaline, smooth and 10 to 25 $\mu$m long with a diameter of 2.5 to 4 $\mu$m. The secondary branches form at a wide angle to the primary branch. The secondary branches are straight or sometimes slightly bent; are hyaline, smooth and are 4 to 7 $\mu$m long with a diameter of 1.5 to 2.5 $\mu$m. Occasionally three levels of branches occur with the intermediate level of branches measuring 12×3 $\mu$m. The conidia are hyaline, smooth or occasionally verrucose and elliptical and 6.0–10.5 (–12)×4.0–8.0 (–9) $\mu$m (CM); chlamydospores are globose, hyaline, thick-walled, 10–35 $\mu$m diameter (on PDA). The culture is characterized by fast growth, white colonies, slightly bent conidiogenous cells, large chlamydospores and conidia which are mostly terminal or lateral but are sometimes intercalary.

*Sporotrichum pruinosum* ATCC 74278 is readily fermented to provide a fermentation broth containing spirolaxine and spirolaxine methyl ether. Cultivation of the fungal culture used in this invention preferably takes place in aqueous nutrient media or on solid media at a temperature of 25 to 30° C., and under stationary aerobic conditions or submerged aerobic conditions with agitation. Nutrient media which are useful for such purposes include a source of assimilable carbon such as sugars, starch and molasses; and a source of organic nitrogen such as casein, enzymatic digests of casein, soybean meal, cottonseed meal, peanut meal and wheat gluten. A source of growth substances such as grain solubles, fish meal and yeast extract as well as salts such as sodium chloride and calcium carbonate and trace minerals such as iron, magnesium, zinc, cobalt and manganese may also be utilized with advantageous results. If excessive foaming is encountered during fermentation, antifoam agents such as vegetable oils or silicones may be added to the fermentation medium. Aeration of the medium in tanks for submerged growth is preferably maintained at the rate of about 0.5 to 2 volumes of free air per volume of broth per minute. Agitation may be maintained by means of agitators generally familiar to those in the field of fermentation. Aseptic conditions must, of course, be maintained throughout the transfer of the microorganism and its growth period.

The microorganism is grown on slants on a suitable growth medium such as PDA for a sufficient period of time to obtain a profuse culture on the growth medium. Generally 10 days to about 21 days are required to obtain sufficient growth to proceed. The slants thus obtained are washed with distilled water and the suspensions thus obtained are homogenized for a sufficient length of time that the homogenate is easily transferable. The homogenate is inoculated into an aqueous nutrient medium in a suitable fermentor, such as shake flasks, Roux bottles, Fernbach flasks or the like. The fermentor is shaken at a temperature of from about 24° C. to about 30° C. for about 2 days to about 14 days. This procedure provides a fermentation broth which contains spirolaxine and spirolaxine methyl ether. The microorganism may also be cultivated on bioassay plates which are filled with 225 milliliters of aqueous media containing 20 grams of agar per liter. The washed suspension is spread over the surface of the agar and the plates are incubated at 24° C. and 85% humidity in an incubator. After 21 to 24 days of incubation, the growth is scraped off the plates and the compound of formula (II) and the compound of formula (I) wherein R is methyl is extracted.

Spirolaxine and spirolaxine methyl ether are isolated from the fermentation broth by extraction of the broth with a suitable organic solvent in which spirolaxine and spirolaxine methyl ether readily dissolve. Thus, the broth is extracted with a suitable extraction solvent such as chloroform, methyl isobutyl ketone, dichloromethane, ethyl acetate, or a solvent system such as ethyl acetate containing 1% methanol. The residue obtained after extraction is partitioned between hexane and acetonitrile and the acetonitrile layer is collected and concentrated to yield a residue which is chromatographed according to the standard methods of organic chemistry well known to one of ordinary skill in the art to afford spirolaxine and spirolaxine methyl ether.

The compounds of this invention of formula (I) wherein R is $(C_2-C_5)$alkyl are prepared by reacting spirolaxine under normal O-alkylation conditions such as the Williamson Reaction. Thus, the compound of formula (II) is dissolved in an alcohol solvent and a $(C_2-C_5)$alkyl halide is added in the presence of a base strong enough to assist the reaction. Generally the reaction is carried out using sodium ethoxide or sodium methoxide, though other bases may also be utilized.

The compounds of this invention of formula (I) wherein R is $CH_3(CH_2)_nCO$— and n is as defined hereinabove are prepared by reacting the compound of formula (II) under normal acylation conditions well known to one of ordinary skill in the art. Thus, the compound of formula (II) is dissolved in aqueous alkali and a suitable acyl halide is added. The preferred aqueous alkali for this reaction is generally sodium hydroxide. The reaction may also be carried out by reacting the compound of formula (II) with an acyl halide in a reaction inert solvent using pyridine to scavenge the hydrogen halide which is formed. Reaction inert solvent means a solvent which does not interact with the reactants, intermediates or products in such a way that adversely affects the yield of the desired products. Suitable reaction inert solvents for this reaction include tetrahydrofuran, toluene, dichloromethane and the like. Particularly preferred is tetrahydrofuran.

The compounds of formula (I) and the compound of formula (II) thus prepared are useful in the treatment of gastric ulcer, duodenal ulcer and gastric cancer. For use in the treatment of conditions of gastric ulcer, duodenal ulcer and gastric cancer in a mammal, including man, an effective amount of a compound of formula (I) or the compound of formula (II) is formulated into a suitable pharmaceutical composition. Depending upon the potency of the particular compound of formula (I) or formula (II) being administered, about 1 mg/kg of body weight per day to about 100 mg/kg of body weight per day, in single or multiple daily doses, is administered to the mammal being treated. A more preferred range is 10 mg/kg of body weight per day to about 40 mg/kg of body weight per day, although in particular cases, at the discretion of the attending physician, doses outside the broader range may be required. The preferred route of administration is generally oral, but parenteral administration (e.g., intravenous, intramuscular, subcutaneous or intramedullary) will be preferred in special cases such as where oral administration is complicated by the patient's inability to ingest the drug.

The compounds of formula (I) and the compound of formula (II) may also be administered in combination with a suitable $H_2$ blocker such as, but not limited to, ranitidine, cimetidine, famotidine, or izatidine or a proton pump inhibitor such as, but not limited to, omeprazole. For use in the treatment of conditions of gastric ulcer, duodenal ulcer and gastric cancer in a mammal, including man, an effective amount of a combination of a compound of formula (I) or the compound of formula (II) and said $H_2$ blocker or said proton pump inhibitor are formulated into a suitable pharmaceutical composition. Depending upon the potency of the combination of the particular compound of formula (I) or formula (II) and said $H_2$ blocker or said proton pump inhibitor being administered, about 1 mg/kg of body weight per day to about 100 mg/kg of body weight per day of the compound of formula (I) or formula (II) along with about 0.1 mg/kg of body weight per day to about 5.0 mg/kg of body weight per day of said $H_2$ blocker or said proton pump inhibitor is administered, in single or multiple daily doses, to the mammal being treated. A more preferred range is 10 mg/kg of body weight per day to about 40 mg/kg of body weight per day of the compound of formula (I) or formula (II) and 0.5 mg/kg of body weight per day to about 3.0 mg/kg of body weight per day of said $H_2$ blocker or proton pump inhibitor, although in particular cases, at the discretion of the attending physician, doses outside the broader range may be required. For example, when said $H_2$ blocker is cimetidine, the preferred dosage for an average, 70 kg adult, is 800 mg twice a day or 1600 mg once a day, at bedtime. The preferred route of administration is generally oral, but parenteral administration (e.g., intravenous, intramuscular, subcutaneous or intramedullary) will be preferred in special cases such as where oral administration of this combination is complicated by the patient's inability to ingest the drug.

The compounds of formula (I) and the compound of formula (II) may also be administered in combination with a suitable $H_2$ blocker such as, but not limited to, ranitidine, cimetidine, famotidine, or izatidine or a proton pump inhibitor such as, but not limited to, omeprazole, and colloidal bismuth subcitrate. For use in the treatment of conditions of gastric ulcer, duodenal ulcer and gastric cancer in a mammal, including man, an effective amount of a combination of a compound of formula (I) or the compound of formula (II), said $H_2$ blocker or said proton pump inhibitor, and colloidal bismuth subcitrate are formulated into a suitable pharmaceutical composition. Depending upon the potency of the combination of the particular compound of formula (I) or formula (II), said $H_2$ blocker or said proton pump inhibitor, and said colloidal bismuth subcitrate being administered, about 1 mg/kg of body weight per day to about 100 mg/kg of body weight per day of said compound of formula (I) or formula (II) along with about 0.1 mg/kg of body weight per day to about 5.0 mg/kg of body weight per day of said $H_2$ blocker or said proton pump inhibitor and about 14 mg/kg of body weight per day to about 56 mg/kg of body weight per day of colloidal bismuth subcitrate is administered, in single or multiple daily doses, to the mammal being treated. A more preferred range is 10 mg/kg of body weight per day to about 40 mg/kg of body weight per day of the compound of formula (I) or formula (II), 0.5 mg/kg of body weight per day to about 3.0 mg/kg of body weight per day of said $H_2$ blocker or said proton pump inhibitor and 14 mg/kg of body weight per day to about 28 mg/kg of body weight per day of said colloidal bismuth subcitrate, although in particular cases, at the discretion of the attending physician, doses outside the broader range may be required. The preferred route of administration of this combination is generally oral, but parenteral administration (e.g., intravenous, intramuscular, subcutaneous or intramedullary) will be preferred in special cases such as where oral administration is complicated by the patient's inability to ingest the drug.

The compounds of formula (I) and the compound of formula (II) may also be administered in combination with a suitable $H_2$ blocker such as, but not limited to, ranitidine, cimetidine, famotidine, or izatidine or a proton pump inhibitor such as, but not limited to omeprazole, and an antibiotic such as, but not limited to amoxicillin and tetracycline. For use in the treatment of conditions of gastric ulcer, duodenal ulcer and gastric cancer in a mammal, including man, an effective amount of a combination of a compound of formula (I) or the compound of formula (II), said $H_2$ blocker or said proton pump inhibitor and said antibiotic are formulated into a suitable pharmaceutical composition. Depending upon the potency of the combination of the particular compound of formula (I) or formula (II), said $H_2$ blocker or said proton pump inhibitor and said antibiotic being administered, about 1 mg/kg of body weight per day to about 100 mg/kg of body weight per day of said compound of formula (I) or formula (II) along with about 0.1 mg/kg of body weight per day to about 5.0 mg/kg of body weight per day of said $H_2$ blocker or said proton pump inhibitor and about 7 mg/kg of body weight per day to about 28 mg/kg of body weight per day of antibiotic is administered, in single or multiple daily doses, to the mammal being treated. A more preferred range is 10 mg/kg of body weight per day to about 40 mg/kg of body weight per day of the compound of formula (I) or formula (II), 0.5 mg/kg of body weight per day to about 3.0 mg/kg of body weight per day of said $H_2$ blocker or said proton pump inhibitor and 14 mg/kg of body weight per day to about 28 mg/kg of body weight per day of said antibiotic, although in particular cases, at the discretion of the attending physician, doses outside the broader range may be required. The preferred route of administration of this combination is generally oral, but parenteral administration (e.g., intravenous, intramuscular, subcutaneous or intramedullary) will be preferred in special cases such as where oral administration is complicated by the patient's inability to ingest the drug.

The compounds of the present invention are generally administered in the form of a pharmaceutical composition comprising at least one of the compounds of formula (I) or formula (II) together with a pharmaceutically acceptable vehicle or diluent. Such compositions are generally formulated in a conventional manner utilizing solid or liquid vehicles or diluents as appropriate to the mode of administration.

For purposes of oral administration, tablets containing excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as, but not limited to, magnesium stearate, sodium lauryl sulfate and talc are often very useful for tableting purposes. Solid compositions of a similar type may also be employed as fillers in soft elastic and hard-filled gelatin capsules; preferred materials in this connection also include, by way of example and not of limitation, lactose or milk sugar as well as high molecular weight polyethylene glycols. When aqueous suspensions and/or elixirs are desired for oral administration, the essential active ingredient may be combined with various sweetening or flavoring agents, coloring matter or dyes and, if so desired, emulsifying and/or suspending agents, together with diluents such as water, ethanol, propylene glycol, glycerin and various like combinations thereof.

The utility of the compounds of the present invention as medicinal agents in the treatment of gastroduodenal disorders such as gastric ulcers, duodenal ulcers or gastric cancer is demonstrated by the activity of said compounds against *Helicobacter pylori* in the in vitro biological screens described hereinbelow. Said screens also provide a means whereby the activities of the compounds of formula (I) can be compared with the activities of other known compounds and treatments. The results of these comparisons are useful for determining dosage levels in mammals, including man, for the treatment of gastroduodenal disorders such as gastric ulcers, duodenal ulcers or gastric cancer.

The compound to be evaluated is solubilized in dimethylsulfoxide (DMSO) and diluted with a sterile brucella broth. Brucella broth is a mixture of pancreatic digest of casein (10 grams), peptic digest of animal tissue (10 grams), yeast extract (2 grams), sodium chloride (5 grams), dextrose (1 gram), sodium bisulfite (0.1 gram) and agar (15 grams) and can be purchased from Acumedia Manufacturers, Inc., Baltimore, Md., 21211, USA. The solubility is noted. The final concentration of dimethylsulfoxide is about 10% of the total volume. Serial two-fold dilutions using an equivalent amount of test compound and brucella broth are then made into sterile brucella broth. An aliquot of each broth dilution within the series is placed in separate sterile petri dishes. Brucella agar, supplemented with about 7% horse blood, is melted and cooled to about 50° C. and then added to the petri dishes such that the final concentration of test compound in the agar is 1:10 and the final concentration of DMSO in the agar is 1%. The agar plates can be prepared and refrigerated overnight one day prior to inoculation with *Helicobacter pylori*.

*Helicobacter pylori* cultures are maintained on trypticase soy-5% sheep blood agar plates, and are transferred every 48 hours. *Helicobacter mustelae* cultures are maintained on the same agar, and are transferred every 48–60 hours, depending upon the heaviness of the growth of the previous transfer. Plates are incubated at 37° C. in GasPak (Becton Dickinson Microbiology Systems, Cockeysville, Md., 21030, USA) jars with CampyPak Plus (Becton Dickinson Microbiology Systems, Cockeysville, Md., 21030, USA) envelopes with palladium catalyst.

Helicobacter cultures are grown in brucella broth supplemented with 10% fetal calf serum in deep petri dishes. The plates are incubated for 18–20 hours at 37° C. in GasPak jars with water-activated CampyPak Plus envelopes with palladium catalyst on a shaker at 50 rpm.

Overnight cultures are diluted ten-fold in brucella broth (no FCS) in screw-capped tubes for use as the standard inoculum. The wells of a Steere's replicator (Craft Machine, Inc., I-95 and Concord Road, Chester, Pa., 19013, USA) are filled with the diluted organism and cells are placed on the agar surface. Inoculated plates are placed in a GasPak jar to which water-activated CampyPak Plus envelopes with palladium catalyst have been added. The jars are incubated at 37° C. for 48 hours. Following incubation, all test plates are compared to a compound-free growth control plate. The minimum inhibitory concentration (MIC) is the concentration which inhibits growth compared to the control plate. A thin film of growth might be visible at higher concentrations but this is discounted, and is not considered to be the true MIC. Control organisms are also inoculated on each plate, and these are diluted 1000-fold for use as inocula. The control organisms include *Campylobacter jejuni*, and the 536G screening cultures of *Escherichia coli, Enterobacter aerogenes, Escherichia cloacae, Providencia stuartii* and *Providencia rettgeri*. Plates and/or inocula transfers are not kept out of a $CO_2$ atmosphere for longer than two hours. All manipulations involving Helicobacter cultures are performed in a laminar flow hood to decrease the chance of contamination of the cultures with mold.

The microdilution broth method described in the Manual of Clinical Microbiology, 4th Edition, E. H. Lennette et al., eds., American Society for Microbiology, Washington, D.C., 1985, pages 973–4 is also used to determine the minimum inhibitory concentration (MIC) of the test compounds.

The abbreviations PDA, MEA, CM, DMSO and FCS, where used herein, mean potato dextrose agar, malt extract agar, corn meal, dimethylsulfoxide and fetal calf serum, respectively. Where used hereinabove and in the claims, the term "mammal" is understood to embrace the term "human."

The present invention is illustrated by the following examples. However, it should be understood that the invention is not limited to the specific details of these examples.

EXAMPLE ONE

A sterile aqueous KF medium having the following composition is prepared:

| KF Medium | |
|---|---|
| Corn Steep Liquor | 5 g |
| Tomato Paste | 40 g |
| Oat flour | 10 g |
| Glucose | 10 g |
| Trace element mix | 10 ml |
| Distilled Water | 1 liter |
| pH adjusted to | 6.8 |

The trace element mix has the following composition:

| | |
|---|---|
| $FeSO_4 \cdot 7H_2O$ | 1.0 g |
| $MnSO_4 \cdot 4H_2O$ | 1.0 g |
| $CuCl_2 \cdot 2H_2O$ | 0.025 g |
| $CaCl_2 \cdot 2H_2O$ | 0.1 g |
| $H_3BO_3$ | 0.056 g |
| $(NH_4)_6Mo_7O_{24} \cdot 4H_2O$ | 0.019 g |
| $ZnSO_4 \cdot 7H_2O$ | 0.2 g |
| 0.6N HCl | 1 liter |

Cells from a 10- to 21- day-old slant of *Chrysosporium pruinosum* ATCC 15155 grown on ATCC medium #336 (PDA) or Difco PDA were washed with 8 mL of sterile distilled water. The suspension was homogenized for two twenty second intervals. Shake flasks containing 50 milliliters of the above-identified KF medium were inoculated with one milliliter each of the homogenized suspension. The flasks were incubated at 28° C. on a shaker at 200 rpm. The culture grew as small pellets. After three days of growth, the seed was blended twice at twenty seconds each and shake flasks containing 50 milliliters each of MPGA (see below for the composition of MPGA solution) were inoculated with one milliliter of the homogenized suspension. The flasks were incubated at 28° C. on a shaker ar 200 rpm. The fermented broths were extracted after 4 to 14 days of incubation.

| MPGA Medium | |
|---|---|
| Malt extract | 40 g/L |
| Peptone | 4 g |
| Glucose | 40 g |
| Agar | 1 g |
| Distilled water | 1 liter |

EXAMPLE TWO

The method of Example One was repeated employing an MPG medium in place of the KF medium. The sterile aqueous MPG medium was prepared having the following composition:

| MPG Medium | |
|---|---|
| Malt extract | 40 g/L |
| Peptone | 4 g |
| Glucose | 40 g |
| Distilled water | 1 liter |

EXAMPLE THREE

A washed slant of *Sporotrichum pruinosum* (ATCC 15155) was inoculated into a side-arm shake flask containing about 300 mL of sterile MPG medium. This seed flask was shaken at 28° C. for three days and aseptically transferred (about 2% inoculum) to a bench top fermentor (New Brunswick BioFlo 4) containing about 15 liters of MPGA medium. The fermentor was maintained at 28° C. with an agitation rate of 500 rpm and an aeration rate of 3 liters of air per minute. The desired component generally appeared at 4 to 6 days into the fermentation and increased significantly at 7 to 9 days. The desired component was obtained by extracting the whole broth with an organic solvent such as ethyl acetate or methyl isobutyl ketone.

EXAMPLE FOUR

Isolation of Spirolaxine and Spirolaxine Methyl Ether

The fermentation broth (14 liters) prepared as described in Example Three hereinabove was extracted with a solution of 1% methanol in ethyl acetate (14 liters). The solvent was evaporated and the residual oil was combined with three other similarly processed extracts. This oil (4.15 g) was partitioned between hexane and acetonitrile. The acetonitrile layer was evaporated to afford 3.26 g of a brown residue. This residue was chromatographed on silica gel (ethyl acetate:hexane::1:1) to afford two fractions. The latter fraction was further chromatographed on silica gel (eluting with a gradient beginning with 100% methylene chloride and increasing polarity to 1% isopropanol in methylene chloride and further increasing polarity to 2.5% isopropanol in methylene chloride) to afford 209 mg of spirolaxine. The earlier fraction was further chromatographed on silica gel (eluting with a gradient beginning with 100% methylene chloride and increasing polarity to 1% isopropanol in methylene chloride) to afford 50.6 mg of spirolaxine methyl ether (the compound of formula (I) wherein R is methyl).

Characterization

1. Spirolaxine: mp 145° C.; $^1$HNMR (CDCl$_3$, δ) 1.16 (1H, dq), 1.25 (3H, d), 1.25 (1H, m), 1.29 (2H, m), 1.33 (1H, m), 1.39 (2H, m), 1.42 (1H, m), 1.42 (1H, m), 1.44 (1H, m), 1.55 (1H, bd), 1.65 (1H, m), 1.68 (2H, m), 1.72 (1H, m), 1.77 (1H, m), 1.82 (1H, m), 1.89 (1H, m), 1.92 (1H, m), 2.14 (1H, m), 3.73 (1H, m), 3.91 (3H, s), 4.17 (1H, ddq), 5.29 (1H, dd), 6.43 (1H, dd),6.46 (1H, d); $^{13}$C NMR (CDCl$_3$, δ) 20.28, 21.21, 24.27, 25.28, 29.33, 30.81, 31.30, 33.55, 34.41, 35.97, 37.97, 55.84, 70.28, 73.91, 80.05, 99.20, 100.42, 105.98, 106.33, 155.11, 159.96, 164.14, 169.29; FABMS 405 m/e (M+H); EIMS 404.21626 m/e.

2. Spirolaxine methyl ether (the compound of formula (I) wherein R is methyl): $^1$HNMR (CDCl$_3$, δ) 1.16 (1H, dq), 1.25 (3H, d), 1.27 (1H, m), 1.32 (1H, m), 1.35 (2H, m), 1.41 (1H, m), 1.42 (1H, m), 1.43 (2H, m), 1.43 (1H, m), 1.53 (1H, bd), 1.64 (1H, m), 1.67 (2H, m), 1.72 (1H, m), 1.74 (1H, m), 1.82 (1H, m), 1.87 (1H, m), 1.99 (1H, m), 2.14 (1H, m), 3.90 (3H, s), 3.96 (3H, s), 4.15 (1H, ddq), 5.30 (1H, dd), 6.40 (1H, dd), 6.42 (1H, d); $^{13}$C NMR (CDCl$_3$, δ) 20.40, 21.27, 24.55, 25.43, 29.35, 30.97, 31.37, 33.53, 34.79, 36.12, 38.01, 55.88, 55.97, 69.94, 73.64, 79.89, 97.40, 98.60, 106.03, 107.01, 155.18, 159.62, 166.65, 168.48; FABMS 419 m/e (M+H).

What is claimed is:

1. A compound of formula (I)

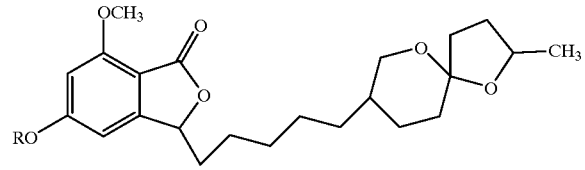

(I)

wherein:

R is (C$_1$–C$_5$) alkyl or CH$_3$(CH$_2$)$_n$CO—; and n is 1, 2, 3 or 4.

2. A compound according to claim 1 wherein R is (C$_1$–C$_5$) alkyl.

3. A compound according to claim 2 wherein R is methyl.

4. A method of treating a mammal suffering from a *Helicobacter pylori* induced disorder, disease or adverse condition comprising administering to said mammal an effective amount of a compound according to claim 1.

5. A method according to claim 4 wherein in said compound R is methyl.

6. A method according to claim 5 wherein said condition is a gastroduodenal disease.

7. A method according to claim 6 wherein said gastroduodenal disease is a duodenal ulcer.

8. A method of treating a mammal suffering from a *Helicobacter pylori* induced disorder, disease or adverse condition comprising administering to said mammal an effective amount of spirolaxine.

9. A method according to claim 8 wherein said condition is a gastroduodenal disease.

10. A method according to claim 9 wherein said gastroduodenal disease is a duodenal ulcer.

11. A pharmaceutical composition comprising an amount of a compound according to claim 1 and a pharmaceutically acceptable carrier.

12. A process for preparing a compound of formula (I),

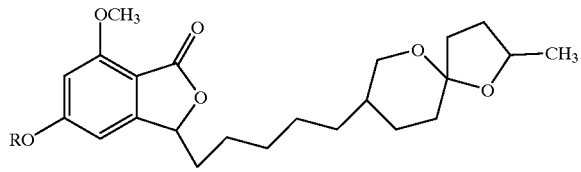

(I)

wherein R is $(C_1-C_5)$ alkyl or $CH_3(CH_2)_nCO$ and n is 1, 2, 3 or 4 comprising, (a) when R is $(C_1-C_5)$ alkyl, reacting a compound of the formula (II),

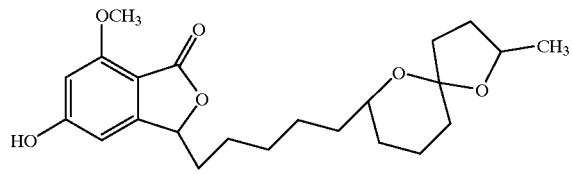

(II)

with a $(C_2-C_5)$alkyl halide in an alcohol solvent in the presence of a base; and (b) when R is $CH_3(CH_2)_nCO$ and n is 1, 2, 3 or 4, reacting a compound of the formula (II), (II)

with an acyl halide in aqueous alkali.

* * * * *